United States Patent
Claus et al.

(10) Patent No.: US 8,425,452 B2
(45) Date of Patent: Apr. 23, 2013

(54) APPLICATION OF A SYSTEM PARAMETER AS A METHOD AND MECHANISM FOR CONTROLLING EYE CHAMBER STABILITY

(75) Inventors: Michael J Claus, Newport Coast, CA (US); Wayne S Wong, Irvine, CA (US); Carina Reisin, Tustin, CA (US); Stephen H Jang, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 226 days.

(21) Appl. No.: 12/639,598

(22) Filed: Dec. 16, 2009

(65) Prior Publication Data

US 2011/0087156 A1    Apr. 14, 2011

Related U.S. Application Data

(63) Continuation of application No. 11/401,529, filed on Apr. 10, 2006, now Pat. No. 7,785,316, which is a continuation-in-part of application No. 11/086,508, filed on Mar. 21, 2005, now Pat. No. 7,670,330.

(51) Int. Cl.
*A61M 1/00* (2006.01)

(52) U.S. Cl.
USPC ............................. 604/35; 604/27; 604/118

(58) Field of Classification Search .......... 604/27, 604/28, 30, 31, 35, 521, 65, 66, 67, 118, 604/119, 120; 606/107
See application file for complete search history.

(56) References Cited

U.S. PATENT DOCUMENTS

| | | | |
|---|---|---|---|
| 4,832,685 A | 5/1989 | Haines | |
| 4,935,005 A | 6/1990 | Haines | |
| 5,032,111 A | 7/1991 | Morris et al. | |
| 5,047,009 A | 9/1991 | Morris et al. | |
| 5,569,188 A | 10/1996 | Mackool | |
| 5,700,240 A | 12/1997 | Barwick et al. | |
| 5,733,256 A | 3/1998 | Costin | |
| 5,865,764 A | 2/1999 | Moorhead | |
| 6,179,808 B1 | 1/2001 | Boukhny et al. | |
| 6,491,661 B1 | 12/2002 | Boukhny et al. | |
| 6,579,255 B2 | 6/2003 | Kadziauskas et al. | |

(Continued)

FOREIGN PATENT DOCUMENTS

| | | |
|---|---|---|
| JP | 62500640 T | 3/1987 |
| JP | 2001161740 A2 | 6/2001 |

(Continued)

OTHER PUBLICATIONS

PCT International Search Report for application No. PCT/US07/66248, Mailed on Aug. 30, 2007, 4 pages.

(Continued)

*Primary Examiner* — Bhisma Mehta (74) *Attorney, Agent, or Firm* — Abbott Medical Optics Inc.

(57) ABSTRACT

A controller for a phacoemulsification system having a handpiece; an irrigation fluid source configured to supply an irrigation fluid to the eye; an aspiration source configured to aspirate the irrigation fluid from the eye through the handpiece; and a controller comprising a duration timer configured to provide a duration of an occlusion, the controller configured to: sense a value of an occlusion indicating parameter corresponding to an occlusion of the handpiece; measure a time since the occlusion of the handpiece; and control the aspiration source to the handpiece based at least in part on the measured time since the occlusion. The occlusion indicating parameter may be a vacuum level, an irrigation flow rate, and/or an aspiration flow rate.

10 Claims, 7 Drawing Sheets

U.S. PATENT DOCUMENTS

| | | |
|---|---|---|
| 6,648,223 B2 | 11/2003 | Boukhny et al. |
| 6,780,166 B2 | 8/2004 | Kanda et al. |
| 7,297,137 B2 | 11/2007 | Gordon et al. |
| 2002/0193817 A1 | 12/2002 | Lal et al. |
| 2003/0050619 A1 | 3/2003 | Mooijman et al. |
| 2003/0105437 A1 | 6/2003 | Neubert |
| 2004/0092921 A1 | 5/2004 | Kadziauskas et al. |
| 2005/0080375 A1 | 4/2005 | Kadziauskas et al. |
| 2005/0118048 A1 | 6/2005 | Traxinger |
| 2005/0209621 A1 | 9/2005 | Gordon et al. |
| 2005/0261628 A1 | 11/2005 | Boukhny et al. |
| 2005/0261715 A1 | 11/2005 | Boukhney et al. |
| 2005/0267504 A1 | 12/2005 | Boukhney et al. |
| 2006/0224107 A1 | 10/2006 | Claus et al. |
| 2006/0224143 A1 | 10/2006 | Claus et al. |

FOREIGN PATENT DOCUMENTS

| | | |
|---|---|---|
| JP | 2001212169 | 8/2001 |
| JP | 2003225256 A2 | 8/2003 |
| WO | WO9945868 A1 | 9/1999 |
| WO | 2004108189 A2 | 12/2004 |
| WO | 2004110524 A2 | 12/2004 |
| WO | 2005037156 A1 | 4/2005 |

OTHER PUBLICATIONS

Office Action mailed Mar. 15, 2011 for Japanese Application No. 2008503035 filed Mar. 14, 2006.

APPLICATION OF A SYSTEM PARAMETER AS A METHOD AND MECHANISM FOR CONTROLLING EYE CHAMBER STABILITY

RELATED APPLICATION

This application is a continuation application of U.S. application Ser. No. 11/401,529, filed on Apr. 10, 2006, now U.S. Pat. No. 7,785,316, issued Aug. 31, 2010, which is a continuation-in-part of U.S. application Ser. No. 11/086,508, filed Mar. 21, 2005, now U.S. Pat. No. 7,670,330, issued Mar. 2, 2010, the entirety of each application is hereby incorporated by reference.

BACKGROUND OF THE INVENTION

1. Field of the Invention

Embodiments of the present invention are generally directed to surgical methods and are more particularly directed to controlling the flow of fluid to and from a patient through a fluid infusion and extraction system such as, for example, in ophthalmic surgery wherein surgical instruments such as electromechanical or pneumatically driven cutters as well as phacoemulsification instruments are commonly employed. These instruments require a source of fluid to infuse a surgical site and a source of negative pressure to evacuate the infused liquid and debris from the site. A pump is usually employed to generate negative pressure. Typical pumps are either flow pumps, such as, for example, peristaltic or scroll pumps, or vacuum pumps, such as, for example Venturi pumps, diaphragm pumps or rotary vane pumps.

2. Description of the Related Art

A number of medically recognized techniques are utilized for cataractic lens removal based on, for example, phacoemulsification, mechanical cutting or destruction, laser treatments, water jet treatments, and so on.

The phacoemulsification method includes making a corneal incision and the insertion of a phacoemulsification handpiece which includes a needle that is ultrasonically driven in order to emulsify, or liquefy, the lens. Concomitantly, fluid is irrigated into the eye and the irrigation fluid and liquefied lens material are aspirated from the eye. Other medical techniques for removing cataractous lenses also typically include irrigating the eye and aspirating lens parts and other liquids. Additionally, some procedures may include irrigating the eye and aspirating the irrigating fluid without concomitant destruction, alteration or removal of the lens.

As is well known, for these various techniques it is necessary to maintain a stable volume of liquid in the anterior chamber of the eye and this is accomplished by irrigating fluid into the eye at the same rate as aspirating fluid and lens material. For example, see U.S. Pat. No. 5,700,240 which is incorporated herewith, in toto, by this specific reference thereto.

During this procedure, it is possible for the aspirating phacoemulsification handpiece to become occluded. This occlusion is caused by particles blocking a lumen or tube in the aspirating handpiece. This blockage can result in increased vacuum (i.e. increasingly negative pressure) in the aspiration line and the longer the occlusion is in place the greater the vacuum. Once the occlusion is cleared, a resulting rush of fluid from the anterior chamber into the aspiration line can outpace the flow of new fluid into the eye from the irrigation source.

The resulting imbalance of incoming and outgoing fluid can create a phenomenon known as post-occlusion surge or fluidic surge, in which the structure of the anterior chamber moves rapidly as fluid is replaced. Such post-occlusion surge may lead to eye trauma. Current precautions against post-occlusion surge cause cataract surgery to be lengthier and more difficult for an attending surgeon.

Alternate surgical procedures, when an occlusion occurs, typically include a reduction of aspiration rate to a level less than the irrigation rate before continuing the procedure. This can be accomplished by changing the aspiration rate setting on the system. This, in turn, allows the pump to run slower and the fluid volume in the anterior chamber to normalize. Other alternate surgical systems may employ a restriction in the aspiration circuit to restrict surge flow when an occlusion clears from the aspiration tube.

Alternative techniques heretofore utilized include a reduction of vacuum on the occlusion by adjusting system settings. This technique often requires an assistant to perform the actual modification of settings.

Still another technique for vacuum control can be accomplished by reducing pressure on a control footpedal or releasing a footpedal altogether. This technique, however, requires a surgeon to discontinue applying ultrasonic power temporarily until the occlusion is either cleared or has been released from the aspirating phacoemulsification handpiece.

A disadvantage in releasing the footpedal is the fact that cataract lens material in the aspirating phacoemulsification handpiece may flow back into the eye chamber.

In addition, the combination of the hereinabove recited techniques may be employed as well. However, once an occlusion occurs, the surgeon must identify the cause and then take corrective action. However, the length of time before the occlusion clears varies. In the time it takes for a surgeon to identify the cause and request corrective action, the occlusion can build sufficient vacuum and then clear, thus resulting in post occlusion surge.

As a result, surgeons tend to operate their phacoemulsification systems at lower vacuum levels than otherwise preferable in order to avoid this problem. The present invention overcomes the disadvantages of operating surgical handpieces, as hereinabove identified.

SUMMARY OF THE INVENTION

A method in accordance with the present invention is directed to operating one or more surgical handpieces including at least 1) an aspiration source, 2) a source of irrigating fluid, and 3) a control unit having a vacuum sensor and/or a flow rate sensor. The aspiration source is typically a flow pump or a vacuum pump, such as, for example, a peristaltic pump or a Venturi pump, respectively, or a combination of the two. One or more of the surgical handpieces may further include a surgical device for cutting, moving, ablating, altering, measuring or treating tissue, and often such surgical devices will require a power source.

Embodiments of the method for application to ophthalmology generally include placing a surgical handpiece in an operative relationship with an eye for a selected surgical procedure. The handpiece may include a phacoemulsification device or an electromechanical, laser, water jet or pneumatically driven cutter suitable for the selected ophthalmic procedures.

A method in accordance with the present invention further includes supplying irrigation fluid from the irrigation fluid source to the eye and providing power from the power source to the handpiece for performing the surgical procedure. In some embodiments, irrigation and aspiration take place without other surgical procedures being applied. Further, some treatments may involve hi-manual processes in which the surgeon uses devices in both hands, such that one device may include, for example, a phacoemulsification mechanism and aspiration source and the other device in the other hand includes an irrigation source, or other combinations thereof.

An aspirating force is applied by the aspirating source through the handpiece in order to aspirate the irrigation fluid from the eye, and during fluid aspiration a vacuum pressure level and/or a flow rate is sensed. Such vacuum pressure and/or flow rate are used in part to detect an occlusion or partial occlusion of the handpiece. As used herein, the term "occlusion" means a partial, complete, or substantially complete blocking of a fluid line, especially an aspiration line, so as to prevent, obstruct, or impede fluid flow into and/or out of the fluid line. As used herein, the term "occlusion" may indicate a total occlusion in which no or substantially no fluid enters and/or exits the fluid line. Alternatively, the term "occlusion" may indicate a partial occlusion in which the fluid line is partially blocked and allows some fluid to enter and/or exit the fluid line, but at a reduced rate as compared to the fluid flow when the occlusion is not present or has been cleared.

More specifically, in accordance with the present invention, a duration of an occlusion is determined from the sensed vacuum level (typically a rise in vacuum pressure, (i.e. an increasingly negative pressure)) and/or a sensed flow rate (i.e. a drop in flow rate for a constant vacuum pressure), and in response thereto, at least one of the 1) supply of irrigation fluid, 2) vacuum level, 3) aspiration rate, and 4) power applied to the handpiece is/are controlled.

More particularly, the vacuum may be controlled by lowering a maximum level of vacuum allowed during an occluded state of a surgical procedure. In addition, a method in accordance with the present invention may include further determining a vacuum drop from the sensed vacuum level and/or a flow rate rise from the sensed flow rate, either or both of which typically indicate a clearance of the occlusion, and in response to the vacuum dropping below and/or flow rate rising above a threshold, increasing the level of aspirating force (i.e. increasing vacuum pressure).

Further, a method in accordance with the present invention may include manipulating an occluding particle with another separate instrument in order to clear the occlusion during the lowered maximum level of vacuum.

Alternatively, in accordance with the present invention during the lowered maximum level of vacuum a supply of irrigation fluid may be varied as well as in combination or separately varying the aspiration rate and in combination or separately varying the power applied to the handpiece.

In one aspect of the invention, a method comprises controlling one or more controlled system parameters (e.g., a vacuum pressure). The method may further comprise selecting an upper value of the one or more controlled system parameters and a lower value of the one or more controlled system parameter. At least one of the one or more controlled system parameters may initially be controlled to be less than or equal to the upper value, for example, prior to the presence of an occlusion in an aspiration line. In an alternative embodiment, at least one of the one or more controlled system parameters may be controlled to be greater than or equal to the lower value, for example, if the controlled system parameter is a flow rate (e.g., of an aspiration or irrigation line) or an absolute pressure of an aspiration line. In yet other embodiments, at least one of the one or more controlled system parameters may be controlled to be between a lower value and an upper value.

The method also comprises sensing a value of an occlusion indicating parameter (e.g., a phaco handpiece parameter such as voltage, current, phase, impedance, mechanical loading of the handpiece, etc.; a fluid parameter such as a temperature, pressure, vacuum level, and/or flow rate of an irrigation or aspiration line, etc.; or a mechanical parameter such as a load, a strain, or temperature of a phaco handpiece, etc.) corresponding to an occlusion of the handpiece. In some embodiments, based at least in part on the sensing of the value of the occlusion indication parameter, a duration of the occlusion is determined. The method additionally comprises controlling the controlled system parameter based at least in part on the sensing of the occlusion indicating parameter and/or the duration of occlusion.

Upon determining that an occlusion has occurred, the controlled system parameter may be controlled to be less than or equal to the previously selected lower value rather than the upper value used prior to the occurrence of the occlusion. In the alternative embodiment mentioned two paragraphs previous, the controlled system parameter is controlled to be greater than or equal to the previously selected upper value, rather than the lower value used prior to the occurrence of the occlusion. In some embodiments, the method further comprises subsequently sensing a fall (or a rise) in the controlled system parameter below a lower threshold (or above an upper threshold) and, in response to the fall (or rise), controlling the controlled system parameter to be less than or equal to the upper value (or greater than or equal lower value).

BRIEF DESCRIPTION OF THE DRAWINGS

The advantages and features of the present invention will be better understood with the following detailed description when considered in conjunction with the accompanying drawings of which.

DETAILED DESCRIPTION OF THE DRAWINGS

Figure 1:
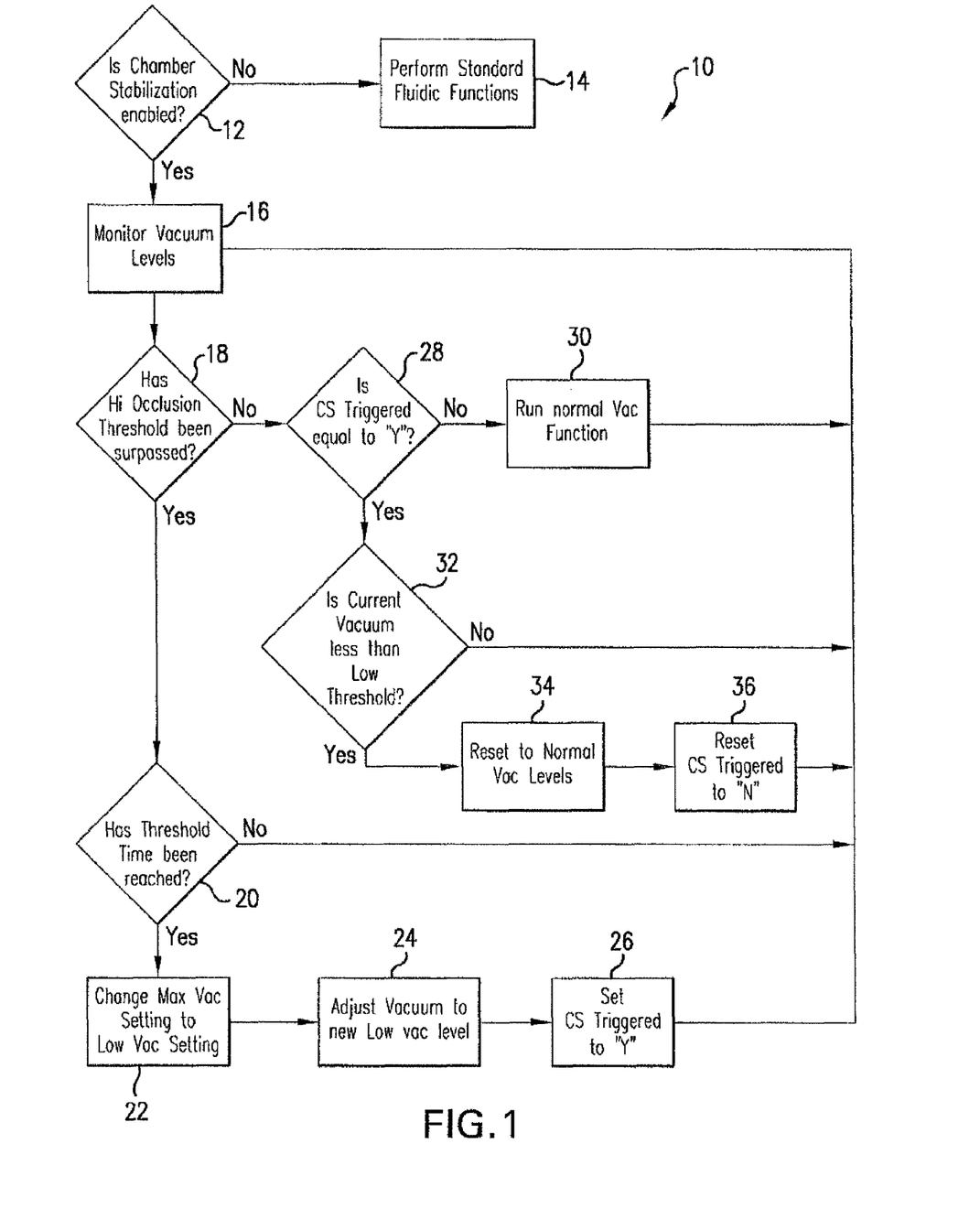
FIG. 1 is a block diagram of one embodiment of the present invention.

As illustrated in FIG. 1, a block diagram 10 sets forth a method in accordance with the present invention. It should be appreciated that the present method applies to controlling at least one of the following system parameters: 1) the supplied irrigation fluid flow rate and/or pressure, 2) aspiration vacuum, 3) aspiration rate, and 4) the power applied to a handpiece in an ophthalmic surgery procedure. As used herein, the term "system parameter" or "parameter" (when in reference to a phacoemulsification system) means any physical characteristic of a system (or a combination of characteristics) that may be sensed, measured, controlled, or used to determine the state of the system or the occurrence of an event, for example the occurrence of an occlusion. The control of only one system parameter is illustrated in the figures for the sake of brevity, that being the vacuum level of an aspiration line. Also, two or more parameters may be controlled and/or sensed simultaneously or sequentially. The aspiration force may be provided by any type of fluid pump, including flow pumps and vacuum pumps.

As shown in FIG. 1, a system or method may include a pre-determined or user-chosen setting (for example, a setting labeled here as "Chamber Stabilization" or "CS") to turn on or off the various embodiments of the present invention. If a user turns off this CS setting (i.e. CS is not enabled (12)), then standard fluidic functions (14) are performed without the benefit of the embodiments described herein.

In accordance with a method of the present invention during surgery employing a flow pump (e.g., peristaltic pump), and if the user sets the system to employ said methods (i.e. CS enabled (12)), vacuum of an aspiration line is monitored (16) and as particles are aspirated, vacuum levels in the aspiration handpiece will fluctuate. When the aspirating handpiece becomes occluded, i.e. partially or fully blocked, vacuum will rise. An occlusion threshold value may be pre-set in the system or entered into the system. In some embodiments, the occlusion threshold value is the value at which the vacuum level is recognized by the system and/or user as indicating that an occlusion has occurred. In other words, as the monitored vacuum increases, the occlusion threshold value is the value of the monitored vacuum at which the aspiration tube has been completely or substantially (e.g., greater than 50%, preferably greater than 80%, and even more preferably greater than 90%) occluded. If vacuum continues to rise until it reaches a maximum allowable vacuum (Max Vac), then the pump is typically stopped. A Max Vac setting may be pre-determined or programmed in the system by a user before or during a surgical procedure. The occlusion threshold may be set at or below the same level as the Max Vac setting. In some embodiments the Max Vac level and occlusion threshold value are set to the same level. Alternately, the occlusion threshold value is set at a percentage (i.e. ≦100%) of the Max Vac level, such as, for example, in a range between about 20% to about 95%. Alternately, the occlusion threshold may be pre-determined at or programmed to a set vacuum level.

A system parameter other than vacuum level of an aspiration line may be used to sense or determine the presence of an occlusion, such as a system or eye temperature, or a flow rate of fluid within an aspiration line or an irrigation line, a pressure within an aspiration line or an irrigation line, and/or a characteristic of the phaco power applied to the handpiece (e.g., a fluid or mechanical load, or an electrical voltage, current, impedance, phase, etc.).

Alternate embodiments for systems using vacuum pumps (e.g., Venturi pumps), flow rate is monitored (not shown in FIG. 1) instead of vacuum level. When the aspirating handpiece becomes occluded, i.e. partially or fully blocked, flow rate will decrease. An occlusion flow rate threshold value may be pre-set in the system or entered into the system. The occlusion flow rate threshold value is the value at which the flow rate is recognized by the system and/or user as indicating that an occlusion has occurred. In other words, as the monitored flow rate decreases, the occlusion flow rate threshold value is the value of the monitored flow rate at which the aspiration tube has been completely or substantially occluded.

In embodiments for combination systems using vacuum pumps and flow pumps, one or both of the vacuum level and flow rate may be monitored and the above-described methods of determining occlusion may be employed.

In any case, when an occlusion occurs (18), the duration of the occlusion is determined (20) in flow pump systems by measuring the amount of time starting from the time when the monitored vacuum rises above the occlusion threshold value and in vacuum pump systems when the monitored flow rate falls below the occlusion flow rate threshold value. After the passing of a programmed or predetermined period of time, (herein referenced as a threshold time ($t_T$)) has elapsed, the maximum allowable vacuum level is automatically reduced (22) to a user programmable new maximum vacuum (Low Vac) level (24). This causes less vacuum around the particle occluding the aspiration handpiece. Reducing vacuum may occur through various known actions, such as, for example: by venting the vacuum; by allowing air or fluid into the vacuum area (e.g., between the occlusion and the pump); by reversing pump flow; and/or by lowering the vacuum setting in the case of vacuum pumps, such as a Venturi pump. The threshold time ($t_T$) is typically in a range between tens of milliseconds and hundreds of milliseconds, and preferably in a range between about 50 milliseconds and about 300 milliseconds. A trigger value (26) may be set to indicate that the maximum allowable vacuum level has been reduced to a lower level (i.e. Low Vac). The system then returns to monitoring vacuum (16) as treatment continues.

During this period of time in which CS is enabled, there has been no change in the surgeon's foot pedal (not shown) position nor has an assistant been required to modify any setting on the system. Accordingly, the method in accordance with the present invention provides the advantage of reducing manual input and accordingly enables the physician to concentrate on the procedure.

The Low Vac level should be set to a level with sufficient vacuum to hold the particle and allow the surgeon to separately or in combination: 1) vary phaco power (or more generally the power to the handpiece surgical mechanism (i.e. laser, cutters, etc.), 2) vary the aspiration rate, and/or 3) vary the irrigation rate as required to clear the occlusion. The method will typically not allow the vacuum level to rise above the low vac level until the occlusion has cleared.

When the occlusion is cleared, the system is operating at or below the Low Vac level, where the potential for post occlusion surge is minimized. In addition, in flow pumps (e.g., peristaltic pumps) after the occlusion is cleared, the actual vacuum level in the aspiration line will drop. In vacuum pumps (e.g., Venturi pumps), the flow rate will rise after the occlusion has cleared. In combination systems using both types of pumps, either or both a vacuum drop or a flow rate increase may be measured after the occlusion is cleared.

In one embodiment in accordance with the present invention, the vacuum drop in a flow-type pump system is identified by determining when it falls below a user programmable or pre-set minimum vacuum threshold (Low Threshold) (32), at which point an original user-programmed maximum allowable vacuum aspiration level (Max Vac) is typically reinstated. In an alternate embodiment employing a vacuum pump, the flow rate increase is identified by determining when the flow rate rises above a user programmable or pre-set minimum flow rate threshold (Low Flow Rate Threshold), at which point an original user-programmed maximum allowable vacuum aspiration level (Max Vac) is typically reinstated. As shown in FIG. 1 for a flow pump system, when the monitored vacuum is below the occlusion threshold value (18), the system checks to determine if Low Vac is set (28), i.e. has the CS trigger been set to "on" or "yes". If not, then normal vacuum and fluid functions are continued (30). If Low Vac is the current setting and the monitored vacuum level is below a Low Threshold (32), Max Vac is re-set (34) and the CS trigger is re-set to "no" or "off" (36). If monitored vacuum is not below Low Threshold, then vacuum monitoring continues based on the Low Vac setting. In vacuum pump embodiments, when monitored flow rate is above the occlusion flow rate threshold, the system checks to determine if Low Vac is set, and if not, then normal vacuum and fluid functions are continued. If Low Vac is the current setting, then Max Vac is re-set. Note that while FIG. 1 primarily depicts embodiments for flow pump systems, it also works for vacuum pump systems if block 16 is changed to include monitoring flow rate, block 18 is changed to include occlusion flow rate threshold, and block 32 is changed to include current flow rate greater than Low Flow. In other embodiments, block 18 may additionally or alternatively include other system parameters, for example the pressure or flow rate in an occlusion line, a system temperature, and/or a parameter of the phaco power, phase, impedance, etc.

Figure 2:
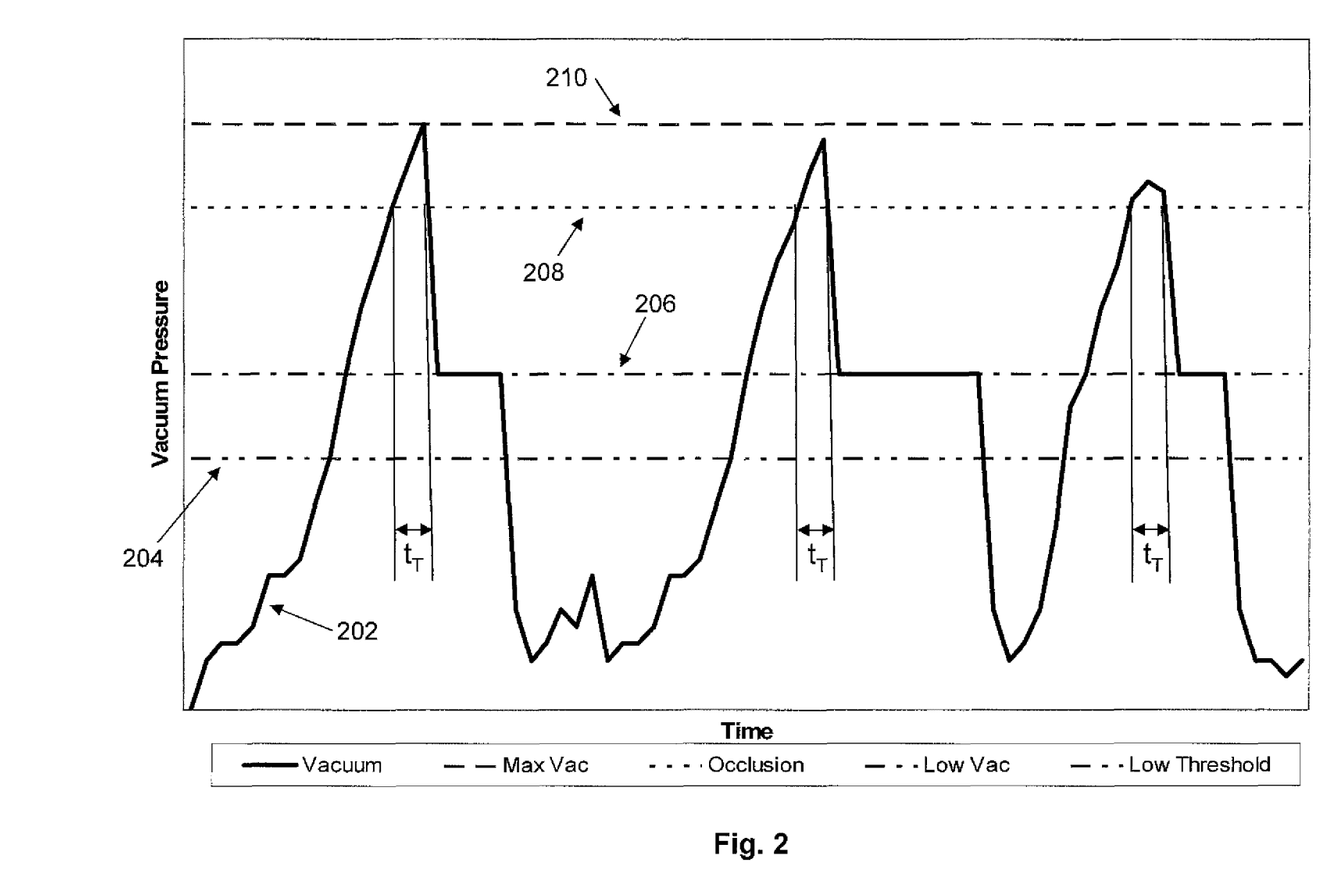
FIG. 2 is a graph showing the vacuum pressure relative to various system settings in an embodiment of the present invention.
Figure 3:
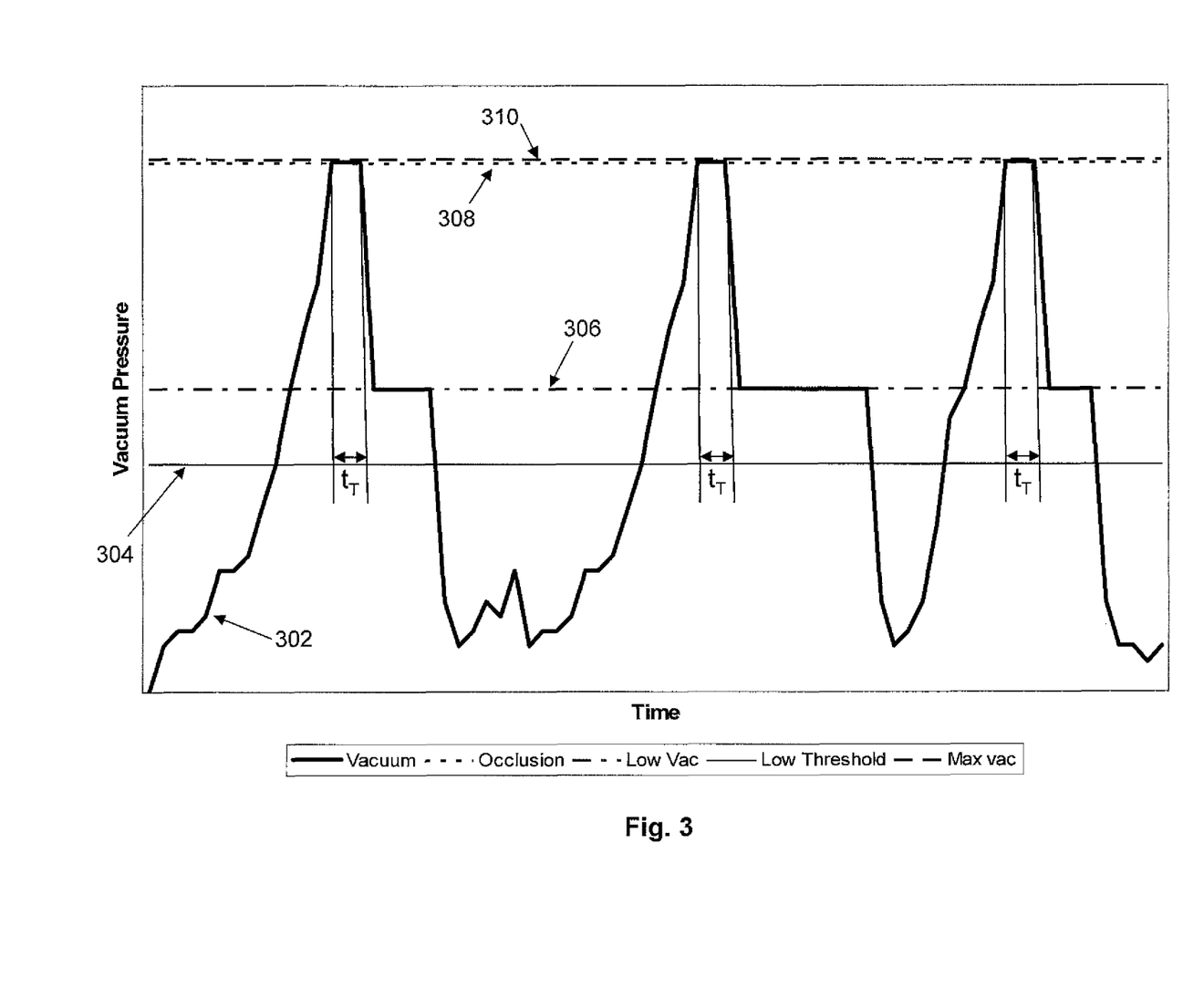
FIG. 3 is a graph showing the vacuum pressure relative to various system settings in an embodiment of the present invention.

FIGS. 2 and 3 depict graphical examples of monitored vacuum levels in accordance with the various embodiments of the present invention. FIG. 2 shows an example in which Max Vac (210) is set at a level above occlusion threshold (208). Low Vac (206) and Low Threshold (204) are also pre-determined or programmed. The monitored vacuum is line 202. Starting at the left side of FIG. 2 and following monitored vacuum 202 to the right, as vacuum 202 rises during a procedure and crosses occlusion threshold 208, the system recognizes that an occlusion has begun and a timer begins measuring the time. If vacuum 202 reaches the Max Vac level (not shown), then the pump may be turned off and the maximum allowable vacuum level may be re-set to Low Vac (206). If Max Vac is not exceeded and once the measured time has passed the threshold time ($t_T$), then the maximum allowable vacuum level is dropped to the Low Vac level (206), thereby reducing the monitored vacuum 202. Alternately, the Low Vac (206) may be set without waiting for a threshold time to pass, in which case a timer would not be needed. As the occlusion is cleared by whatever means, vacuum 202 begins to drop again until it falls below Low Threshold (204). At that point, the system recognizes that the occlusion has been cleared, and Max Vac is re-set as the maximum allowable vacuum level. The monitored vacuum level 202 typically stays at the lower level in flow pump systems until another occlusion is encountered. When another occlusion is encountered, the vacuum 202 begins to rise again and the process stated above begins anew.

FIG. 3 shows a similar example to that of FIG. 2, with the difference that the Max Vac value (310) and the occlusion threshold value (308) are pre-determined or programmed at or very near the same level. Low Vac (306) and Low Threshold (304) are also pre-determined or programmed. The monitored vacuum line on the graph is 302. Starting at the left side of FIG. 3 and following monitored vacuum 302 to the right, as vacuum 302 rises during a procedure and reaches occlusion threshold 308 and/or Max Vac level 310, the system recognizes that an occlusion has occurred and a timer begins measuring the time. Additionally, the pump is typically turned off and the maximum allowable vacuum level is re-set to Low Vac (306), thereby reducing the monitored vacuum 302. In some embodiments, the Low Vac is not set until the threshold time has been reached. Alternately, the Low Vac may be set without waiting for a threshold time to pass, in which case a timer would not be needed. As the occlusion is cleared by whatever means, vacuum 302 begins to drop again until it falls below Low Threshold (304). At that point, the system recognizes that the occlusion has been cleared, and Max Vac (310) is re-set as the maximum allowable vacuum level. The monitored vacuum level 302 typically stays at the lower level in flow pump systems until another occlusion is encountered. When another occlusion is encountered, the vacuum 302 begins to rise again and the process stated above begins anew.

Note that graphical representations of embodiments including vacuum pumps wherein flow rate is sensed and used to control vacuum generally look like inverted versions of FIGS. 2 and 3 with the y-axis showing flow rate and without a Max Vac value.

The above embodiments and examples describe two vacuum levels (i.e. Max Vac and Low Vac), however other embodiments may include various intermediate levels and settings. For example, a middle vacuum level (Mid Vac) between Max Vac and Low Vac could be pre-determined or programmed. In such an embodiment, once monitored vacuum has risen above occlusion threshold for a set threshold period of time, the maximum allowable vacuum level is set to Mid Vac. If the occlusion is not cleared at Mid Vac after a second threshold period of time, then the maximum allowable vacuum level is set to Low Vac and held there until the occlusion is cleared. After occlusion clearance (i.e. once monitored vacuum has fallen below a Low Threshold), then the maximum allowable vacuum level may be re-set to either Mid Vac or Max Vac. By having one or more intermediate vacuum levels, a user has more control over the vacuum levels as well as the potential surge characteristics once an occlusion is cleared. In one embodiment, once an occlusion has been determined, the system may automatically begin lowering the maximum allowable vacuum level incrementally by pre-determined or programmed increments until the occlusion is cleared. In this latter embodiment, the vacuum could be maintained as close to Max Vac as possible throughout the procedure. As described above, these alternate embodiments are equally applicable to flow pump systems, vacuum pump systems, or combination pump systems.

More generally, embodiments of the invention may be applied to any appropriately selected system parameter (parameter of a phacoemulsification system), for example, to sense the presence of an occlusion and/or to be controlled once an occlusion has been detected. For example, the presence of an occlusion in an aspiration line may be determined based on a decrease in an irrigation flow (rather than being based on a vacuum pressure in an aspiration line, as illustrated in FIGS. 2 and 3). In general, any one or a combination of system parameters may be used either to sense an occlusion or be controlled once an occlusion is sensed or detected, including, but not limited to, aspiration flow/pressure, irrigation flow/pressure, and/or one or more phaco parameters (e.g., voltage, current, phase, impedance, mechanical loading of the handpiece, etc.). By controlling one or more system parameters in response to the occurrence of the occlusion, damage to the eye during a surgical procedure may be prevented or mitigated.

Figure 4:
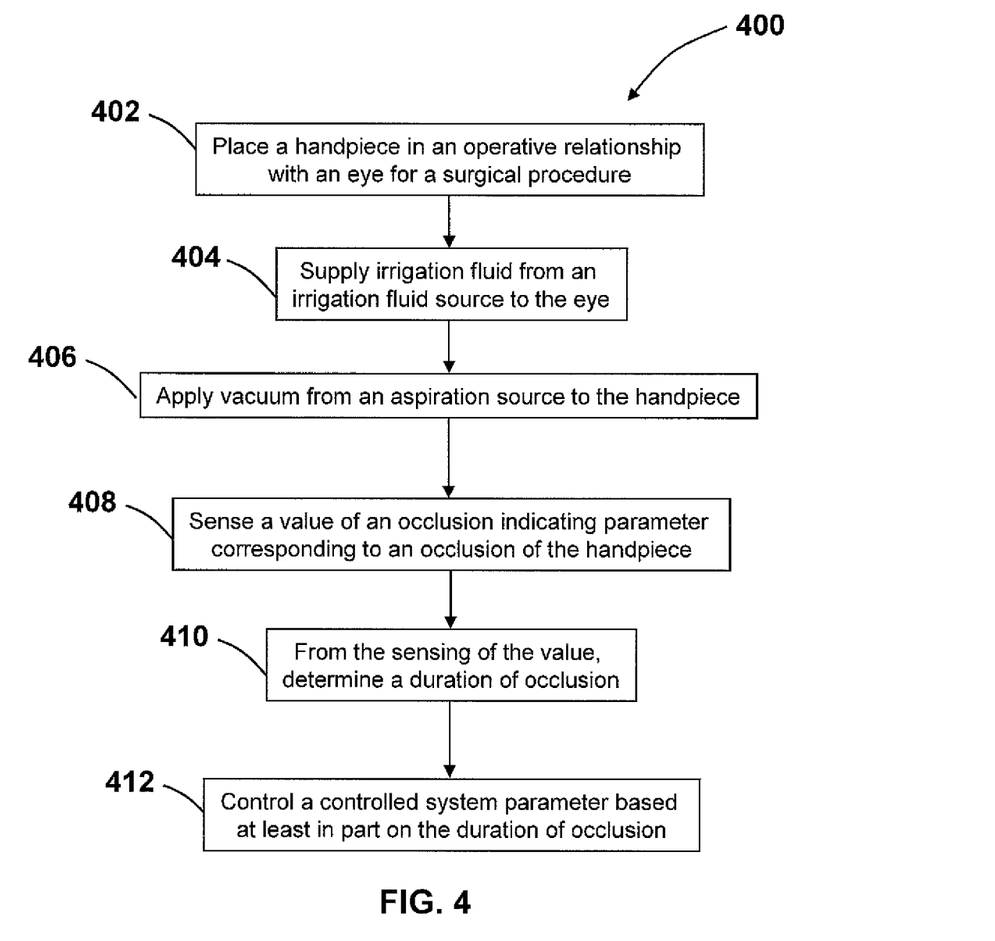
FIG. 4 is a method according to embodiments of the invention operating a surgical handpiece.

Accordingly, as illustrated in FIG. 4, in certain embodiments, a method 400 of operating a surgical handpiece includes an operational block 402, placing a handpiece in an operative relationship with an eye for a surgical procedure. The method 400 also includes an operational block 404, supplying irrigation fluid from an irrigation fluid source to the eye. The method 400 further includes an operational block 406, applying vacuum from an aspiration source to the handpiece in order to aspirate the irrigation fluid from the eye through the handpiece. The method 400 additionally comprises an operational block 408, sensing a value of an occlusion indicating parameter corresponding to an occlusion of the handpiece. Then at an operational block 410, based on the sensing of the value, determining a duration of occlusion. The method 400 also comprises an operational block 412, controlling a controlled system parameter based at least in part on the duration of occlusion.

Figure 5:
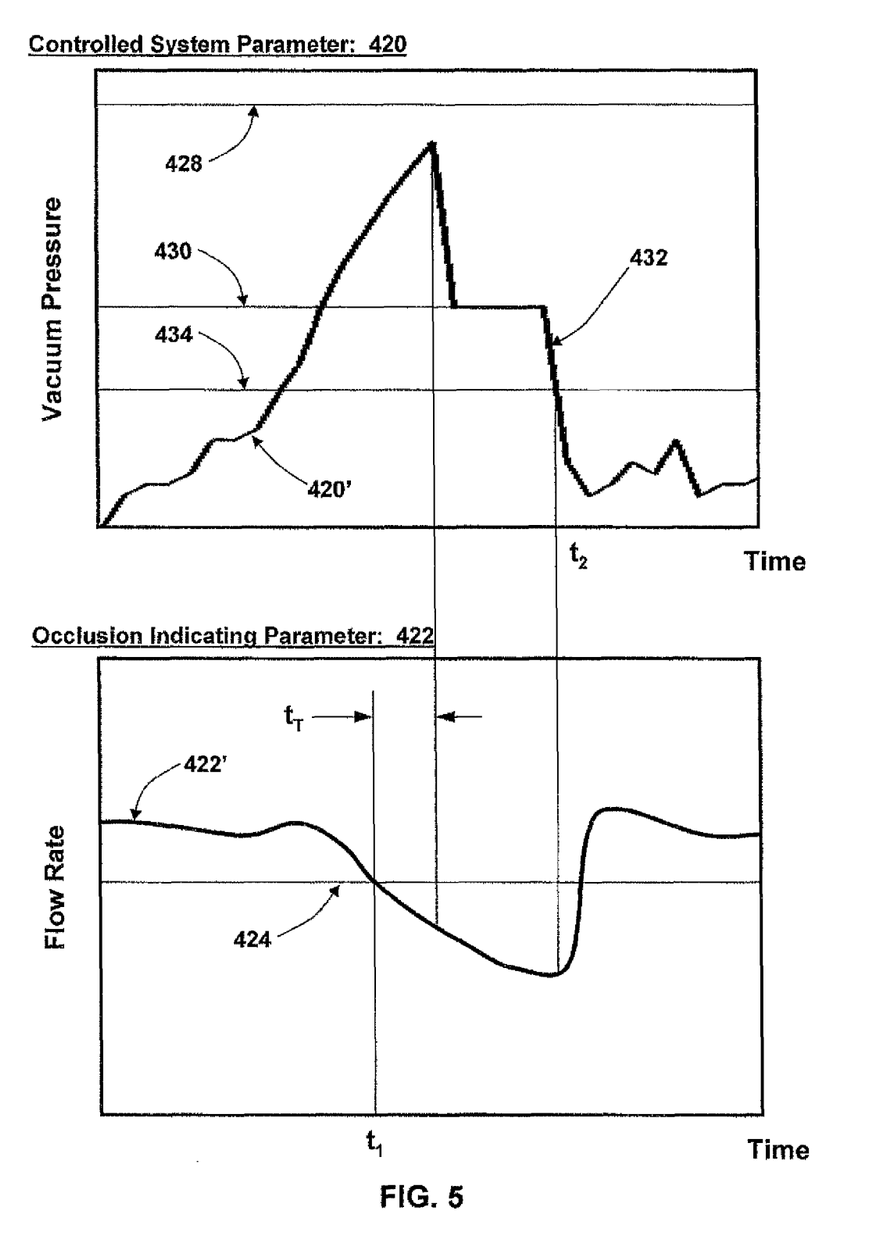
FIG. 5 is a pair of graphs illustrating one embodiment of the method shown in FIG. 4

With additional reference to FIG. 5, an example of the method 400 is shown for a hypothetical case in which a controlled system parameter 420 (in this case the vacuum pressure 420' shown in the upper graph of FIG. 5) of a phacoemulsification system is controlled based, at least in part, on the value of an occlusion indicating parameter 422 (in this case the flow rate 422' shown in lower graph of FIG. 5, for example an irrigation flow or an aspiration flow). The parameters 420, 422 may be sensed using transducers located, including but not limited to, one or more sensors in the console of the phacoemulsification system, one or more sensors in a handpiece, at some location along a line connecting the console and the handpiece, or in a line connected to the console, handpiece, or the line therebetween.

In certain embodiments, the occlusion indicating parameter 422 may be selected to indicate a complete (100%) or substantially complete (greater than ~95%) occlusion of a fluid line, such as an aspiration line. In other embodiments, the occlusion indicating parameter 422 may be selected to indicate a partial occlusion of a fluid line. For example, the occlusion indicating parameter 422 may be selected to indicate an aspiration line has a level of occlusion that is greater than or equal to 10%, 25%, 50%, 75%, or 90%. Where the level of occlusion indicates an approximate percent reduction in the fluid flow entering and/or exiting aspiration line as compared to a condition in which there is no occlusion or substantially no occlusion present or an occlusion has just been cleared.

With continued reference to FIG. 5 and starting at the left side of the upper graph, the vacuum pressure 420' initially has a relatively low vacuum pressure and is controlled in any event to be less than or equal to an upper value or limit 428. In an alternative embodiment (not shown), a different controlled parameter 420 is controlled to be greater than or equal to a lower value or limit, for example if the controlled parameter 420 were an absolute pressure (e.g., where "zero pressure" is equal to a complete vacuum) of the aspiration line.

In the illustrated embodiment shown in the lower graph of FIG. 5, the presence of an occlusion is sensed or detected when the sensed value of the occlusion indicating parameter 422 is less than or equal to a predetermined value 424. In other embodiments, an occlusion is sensed or detected when the occlusion indicating parameter 422 is greater than or equal to a predetermined parameter. In yet other embodiments, the existence of an occlusion may be determined based on two or more occlusion indicating parameters 422, either based on their individual values or based on some predetermined condition or relationship between the two parameters. For example, in the illustrated embodiment, the presence of an occlusion may be determined based on the irrigation flow rate being less than or equal to the predetermined value 424, based on the vacuum pressure of the aspiration line exceeding the upper level or limit 428, or based on some combination thereof.

Referring to operational block 410 of the method 400, once the existence of an occlusion has been sensed or determined to have occurred, a duration of the occlusion is determined. The duration of the occlusion may be determined using means such as a countdown timer or a software algorithm, among others. When the duration of the occlusion reaches a predetermined value $t_T$, for example as illustrated in the graphs of FIG. 5, the vacuum pressure 420' may be controlled based on the duration of occlusion attaining or exceeding the predetermined value $t_T$. In the illustrated embodiment, the vacuum pressure 420' is controlled to be less than or equal to a lower value or control limit 430 (rather than being controlled to be less than or equal to the upper limit 428, which was the control limit prior to the occlusion). In an alternative embodiment (not shown), a controlled system parameter 420 is controlled to be greater than or equal to an upper value, for example if the controlled parameter 420 were an absolute pressure of the aspiration line. Additionally or alternatively, the controlled system parameter 420 may comprise controlling any system parameter that serves to provide a desired outcome during the surgical procedure. For example, the controlled system parameter 420 may comprise temperature or a phaco power parameter that is increased or decreased in accordance with a predetermined algorithm so as to avoid damaging the eye during or immediately after an occluded condition.

Referring to top graph in FIG. 5, the method 400 may further comprise sensing a drop 432 in the vacuum pressure 420' below a lower threshold 434 and, in response to the drop 432, once again controlling the vacuum pressure 420' to be less than or equal to the upper value 428. The appropriate drop 432 to trigger this change is shown in FIG. 5 to occur at a time $t_2$. Alternatively, for example where a controlled parameter 420 is a flow rate in a vacuum pump system, the method 400 may further comprise sensing a rise in the controlled system parameter 420 above an upper threshold and, in response to the rise, controlling the controlled parameter 420 to be greater than or equal to a lower value.

The parameters 420, 422 may, as appropriate, be any single system parameter of the phacoemulsification system or a combination of the system parameters (e.g., one or more of a vacuum level, a supply irrigation pressure, a supply irrigation flow rate, an aspiration pressure or rate, or a phaco parameter such as the power applied to the handpiece). The parameters 420, 422 may be different system parameters, as in the illustrated in FIG. 5, or a single, common system parameter, similar to the situation illustrated in FIGS. 2 and 3.

In some embodiments, the controlled system parameter 420 is the pressure of a pressurized infusion system, for example, as discussed in U.S. Pat. Nos. 5,032,111 and 5,047,009, herein incorporated by reference. In other embodiments, the controlled system parameter 420 is the expansion or contraction of an expandable bladder or control volume that is used to increase and/or decrease the capacity of an irrigation line to supply fluid flow into the eye (for example after an occlusion has broken and the aspiration flow suddenly increases). Such an arrangement is disclosed, for example, in U.S. Patent Application Publication Number 2005/0080375, which is herein incorporated by reference.

Figure 6:
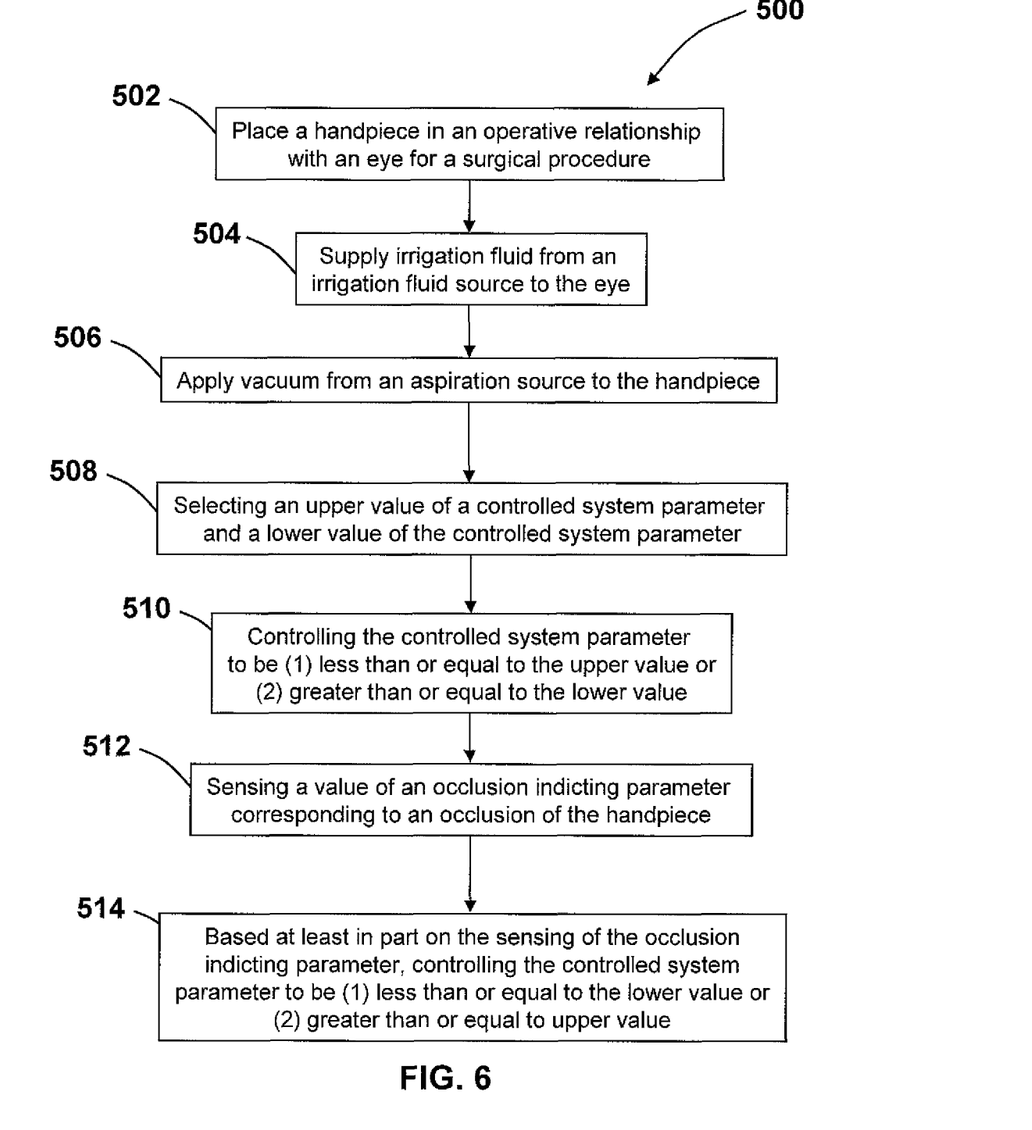
FIG. 6 is another method according to embodiments of the invention operating a surgical handpiece.

In certain embodiments, the controlled system parameter 420 may be controlled to be above or below one or both of two predetermined levels, depending on whether or not an occlusion has been detected or sensed. For example, as illustrated in FIG. 6, a method 500 of operating a surgical handpiece comprises an operational block 502, placing a handpiece in an operative relationship with an eye for a surgical procedure. The method 500 also comprises an operational block 504, which includes supplying irrigation fluid from an irrigation fluid source to the eye. The method 500 further comprises an operational block 506, applying vacuum from an aspiration source to the handpiece in order to aspirate the irrigation fluid from the eye through the handpiece. The method 500 additionally comprises an operational block 508, selecting an upper value of a controlled system parameter 420 and a lower value of the controlled system parameter 420. The method 500 further comprises an operational block 510, controlling the controlled system parameter 420 to be (1) less than or equal to the upper value (e.g., when the controlled system parameter 420 is the vacuum pressure 420') and/or (2) greater than or equal to the lower value (e.g., when the controlled system parameter 420 is an absolute pressure or a flow rate). The method 500 additionally comprises an operational block 512, sensing a value of the occlusion indicting parameter 420 corresponding to an occlusion of the handpiece. The method 500 also comprises an operational block 514, based at least in part on the sensing of the occlusion indicting parameter 422, controlling the controlled system parameter 420 to (1) less than or equal to the lower value (when criteria (1) of block 510 is used) or (2) greater than or equal to upper value (when criteria (2) of block 510 is used).

For example, referring again to upper graph of FIG. 5, it will be appreciated that prior to detection of an occlusion at time $t_1$, the vacuum pressure 420' of the aspiration line is controlled to be less than or equal to the upper value 428. At a time $t_T$ after detection of the occlusion, the vacuum pressure 420' is controlled to be less than or equal to the lower value 430. In other embodiments of the method 500, a controlled system parameter 420 is controlled to be less than or equal to a lower value as soon as an occlusion is detected, rather than waiting for a certain delay time. In yet other embodiments, some other criteria may be used in addition to the detection of an occlusion for determining whether the controlled system parameter is to be above or below an upper value or a lower value.

Figure 7:
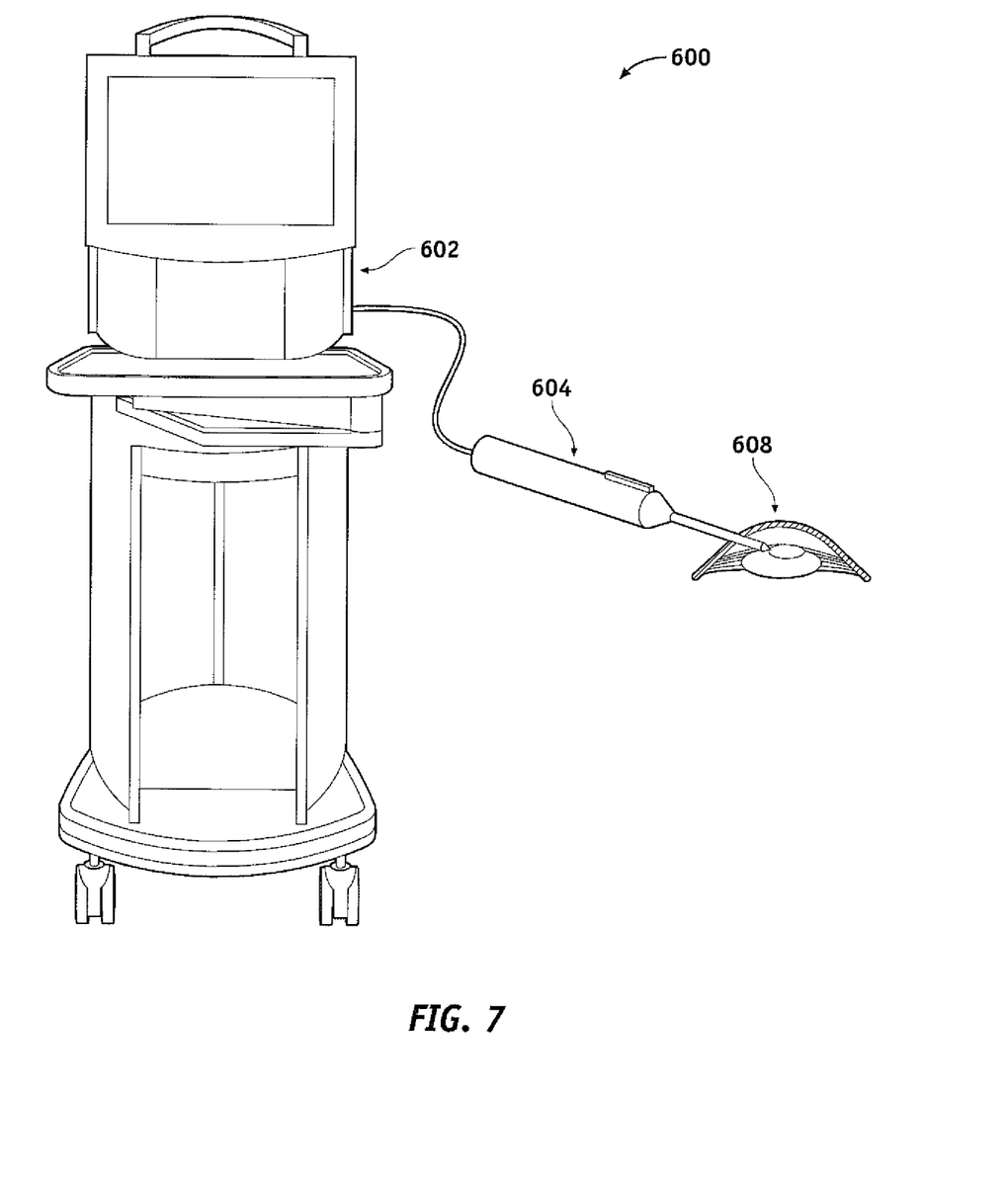
FIG. 7 is a perspective view of a phacoemulsification system according to embodiments of the present invention.

Referring to FIG. 7, in certain embodiments, one or more of the methods discussed herein may be incorporated into a phacoemulsification system 600 and/or a controller 602 for a handpiece 604. For example, in certain embodiments, the phacoemulsification system 600 comprises a handpiece 604, an irrigation fluid (not shown), an aspiration source (not shown), and the controller 602. The handpiece 604 is configured to be placed in an operative relationship with an eye 608 for a surgical procedure. The irrigation fluid is configured to supply an irrigation fluid source to the eye 608. The aspiration source is configured to apply a vacuum to the handpiece 604 in order to aspirate the irrigation fluid from the eye 608 through the handpiece 604. In certain embodiments, referring again back to FIG. 5, the controller 602 may be configured to control vacuum pressure 420' to be less than or equal to the upper value 428. The controller 602 is additionally configured to sense the value 424 of the occlusion indicating parameter 422 corresponding to an occlusion of the handpiece 604 and, from the sensing of the value 424, determine a duration of occlusion. The controller is also configured to control a controlled system parameter to be less than or equal to the lower value 430 based at least in part on at least one of (1) the sensing of the occlusion indicating parameter 422 and (2) the duration of occlusion.

One advantage of the embodiments described above is that surgeons can more safely and effectively utilize the full range of aspiration rates, vacuum pressures and flow rates available on typical surgical devices. For example, in typical phacoemulsification devices, the aspiration mechanisms may allow for vacuum or suction pressures during normal operation up to 650 mmHg or more. Typical current suction pressures may be in the range of 300 mmHg. Often, surgeons use the low end or middle of the available aspiration ranges in order to avoid unsafe fluidic surges during occlusion events. However, this means that they are typically treating at a slower rate because of the reduced aspiration flow. By utilizing the present invention, higher aspiration rates and vacuum levels may be used without fear of dangerous fluidic surges.

Methods and systems in accordance with the present invention may be incorporated into or include software routines and modules and/or hardware and firmware in order to automatically carry out one or more of methods discussed above. An input device, such as, for example, a mouse or keyboard, may be included in the system to facilitate user input of parameters and settings. Further, various storage media, such as, for example, CDs, DVDs, tape storage, magnetic, optical or electronic storage media, or other known storage media may be included to store settings.

Although there has been hereinabove described specific applications of vacuum and irrigation pressure as a method and mechanism for controlling eye chamber stability in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. The methods and embodiments of the present invention have generally been discussed with reference to ophthalmology. However, the methods and embodiments have equal application to other medical arts, including those in which irrigation and aspiration are used in the excision, removal, movement, treatment, measurement and so on of tissue. Accordingly, any and all modifications, variations or equivalent arrangements which may occur to those skilled in the art, should be considered to be within the scope of the present invention as defined in the appended claims.

What is claimed is:

1. A phacoemulsification system, comprising:
a handpiece configured to be placed in an operative relationship with an eye for a surgical procedure;
an irrigation fluid source configured to supply an irrigation fluid to the eye;
an aspiration source configured to aspirate the irrigation fluid from the eye through the handpiece; and
a controller comprising a duration timer configured to determine a duration of an occlusion of the handpiece, the controller configured to:
sense a value of an occlusion indicating parameter corresponding to an occlusion of the handpiece;
measure a time since the occlusion of the handpiece using the duration timer; and
once the time since the occlusion exceeds a predetermined value, control the aspiration source to aspirate fluid from the handpiece at a level bounded by a control limit that is less than a maximum limit based at least in part on the measured time since the occlusion.

2. The system of claim 1, wherein the occlusion indicating parameter is a vacuum level.

3. The system of claim 1, wherein the occlusion indicating parameter is at least one selected from the group consisting of an irrigation flow rate and an aspiration flow rate.

4. The system of claim 1, wherein controlling the aspiration source to the handpiece comprises reducing a vacuum level in the handpiece.

5. The system of claim 1, wherein controlling the aspiration source to the handpiece comprises reducing vacuum applied from the aspiration source after the measured time exceeds a predetermined value.

6. A phacoemulsification system, comprising:
a handpiece configured to be placed in an operative relationship with an eye for a surgical procedure;
an aspiration source configured to aspirate irrigation fluid from the eye through the handpiece; and a controller configured to:
- determine a time an occlusion of the handpiece occurs;
- sense a value of an occlusion indicating parameter corresponding to the occlusion of the handpiece;
- measure a time since the occlusion of the handpiece; and
- once the time since the occlusion exceeds a predetermined value, control the aspiration source to aspirate fluid from the handpiece based at least in part on the measured time since the time the occlusion of the handpiece occurred.

7. The system of claim 6, wherein the occlusion indicating parameter is a vacuum level.

8. The system of claim 6, wherein the occlusion indicating parameter is at least one selected from the group consisting of an irrigation flow rate and an aspiration flow rate.

9. The system of claim 6, wherein controlling the aspiration source to the handpiece comprises reducing a vacuum level in the handpiece.

10. The system of claim 6, wherein controlling the aspiration source to the handpiece comprises reducing vacuum applied from the aspiration source after the measured time exceeds a predetermined value.

\* \* \* \* \*